United States Patent
Bernabeu Wittel et al.

(10) Patent No.: US 10,960,011 B2
(45) Date of Patent: Mar. 30, 2021

(54) COMPOSITIONS FOR THE TREATMENT OF ISCHEMIC ULCERS AND STRETCH MARKS

(71) Applicant: SERVICIO ANDALUZ DE SALUD, Seville (ES)

(72) Inventors: José Bernabeu Wittel, Seville (ES); Raquel Cabrera Fuentes, Seville (ES)

(73) Assignee: SERVICIO ANDALUZ DE SALUD, Seville (ES)

(*) Notice: Subject to any disclaimer, the term of this patent is extended or adjusted under 35 U.S.C. 154(b) by 0 days.

(21) Appl. No.: 16/312,898

(22) PCT Filed: Jun. 23, 2017

(86) PCT No.: PCT/ES2017/070460
§ 371 (c)(1),
(2) Date: Dec. 21, 2018

(87) PCT Pub. No.: WO2017/220845
PCT Pub. Date: Dec. 28, 2017

(65) Prior Publication Data
US 2019/0321372 A1 Oct. 24, 2019

(30) Foreign Application Priority Data
Jun. 23, 2016 (ES) ................. ES201630856

(51) Int. Cl.
*A61K 31/554* (2006.01)
*A61P 9/10* (2006.01)
*A61K 8/49* (2006.01)
*A61Q 19/00* (2006.01)

(52) U.S. Cl.
CPC .............. *A61K 31/554* (2013.01); *A61K 8/49* (2013.01); *A61P 9/10* (2018.01); *A61Q 19/00* (2013.01)

(58) Field of Classification Search
CPC .................................. A61K 31/554; A61P 9/10
See application file for complete search history.

(56) References Cited

U.S. PATENT DOCUMENTS

| | | |
|---|---|---|
| 2019/0308956 A1 | 10/2019 | Sánchez Céspedes et al. |
| 2019/0358467 A1 | 11/2019 | Velázquez et al. |
| 2019/0365675 A1 | 12/2019 | Orío Ortiz et al. |
| 2020/0055808 A1 | 2/2020 | Vega et al. |
| 2020/0281897 A1 | 9/2020 | Pérez et al. |

FOREIGN PATENT DOCUMENTS

| | | |
|---|---|---|
| EP | 1 516 622 A1 | 3/2005 |
| WO | 2013/119984 A1 | 8/2013 |

OTHER PUBLICATIONS

Bansal et al., "Comparative Evaluation of 0.2% Glyceryl Trinitrate vs. 2% Diltiazem Ointment in Treatment of Chronic Anal Fissure Treatment—A Randomized Trial," *Hellenic Journal of Surgery* 88(1):25-30, 2016.

Elsaie et al., "Striae Distensae (Stretch Marks) and Different Modalities of Therapy: An Update," *Dermatol Surg* 35:563-573, 2009.

Fernández García et al., "Efficacy and safety of topical diltiazem 2% in anal fissure," *Farm Hosp.* 33(2):80-88, 2009.

Hermanns et al., "High-resolution epiluminescence colorimetry of striae distensae,"*JEADV* 20:282-287, 2006.

Jonas-Obichere et al., "Anal Fissure," *Surgery* 21(7):168-170, 2003.

Puche et al., "Local treatment of a chronic anal fissure with diltiazem vs. nitroglycerin. A comparative study," *CIRUGÍA ESPAÑOLA* 87(4):224-230, 2010.

Nitsche, "Raynaud, Digital Ulcers and Calcinosis in Scleroderma," *Reumatol Clin* . 8(5):270-277, 2012.

Tiernan et al., "Benign anal conditions: haemorrhoids, fissures, perianal abscess, fistula-in-ano and pilonidal sinus," *Surgery* 29(8):382-386, 2011.

Ud-Din et al., "Topical management of striae distensae (stretch marks): prevention and therapy of striae rubrae and albae," *JEADV* 30: 211-222, 2016.

*Primary Examiner* — Bruck Kifle
(74) *Attorney, Agent, or Firm* — Seed Intellectual Property Law Group LLP

(57) ABSTRACT

The invention relates to compositions used to relieve, improve, prevent and/or treat stretch marks and/or skin ulcers preferably of ischemic origin. The invention also relates to the composition, dosage form and uses thereof.

11 Claims, 3 Drawing Sheets

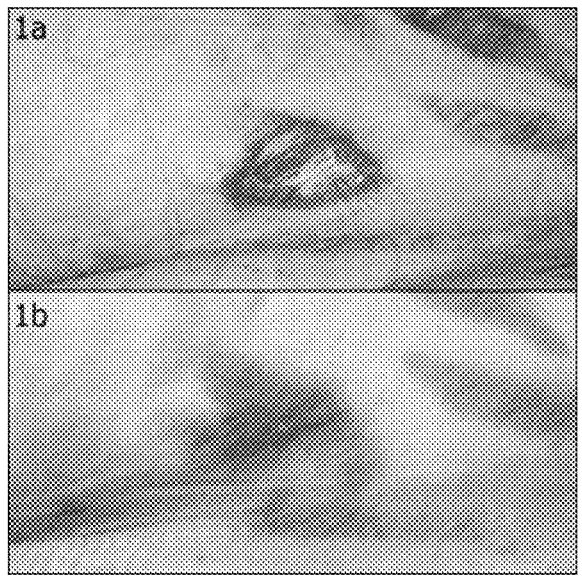
Fig. 1 (A and B)
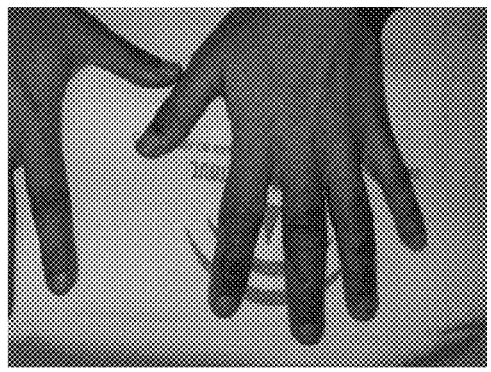
→  →  Fig. 2A
Fig. 2B

COMPOSITIONS FOR THE TREATMENT OF ISCHEMIC ULCERS AND STRETCH MARKS

FIELD OF THE INVENTION

The present invention is comprised in the field of medicine and pharmacy, and relates to the use of benzothiazepines, their pharmaceutically acceptable salts, solvates, and hydrates in the production of medicinal products used to treat stretch marks and ulcers, preferably skin ulcers and specifically ulcers of ischemic origin.

BACKGROUND OF THE INVENTION

Successful treatment of striae distensae (SD or stretch marks) has always been a challenge. Nardelli offered the first morphologically correct description of these lesions in 1936, when said author classified them as striae atrophicae. The exact origin of stretch marks is still unknown, and the factors responsible for the development thereof are still not understood. While the causes of SD are not clear, several theories have been proposed (Elsaie et al., 2009. *Dermatol Surg* 35: 563-573).

High-resolution epiluminescence colorimetric assessment of SD has identified four different types: striae alba, striae rubra, striae caerulea, and striae nigra. The direct and indirect influences of melanocyte mechanobiology seem to have a significant effect on the different colors of SD (Pierard & Hermans 2006. JEADV 20: 282-7). The histology of stretch marks is that of a scar, and the development of SD has been likened to that of wound healing or scar formation. In the early stages, inflammatory changes may be conspicuous, but later the epidermis is thin and flattened. Recent SD show a deep and superficial perivascular lymphocytic infiltrate around the venules.

Collagen bands on the upper third of the reticular dermis are stretched and aligned parallel to the surface of the skin. In the latter stages, there is thinning of the epidermis due to flattening of the rete ridges and loss of collagen and elastin.

Some of the different hypotheses in the literature on the development of SD include:
1. Infection leads to the release of striatoxin which damages tissues by way of a microbial toxin.
2. The mechanical effect of stretching, which can lead to the rupture of connective tissue structure (for example, pregnancy, obesity, weightlifting).
3. Normal growth as seen in adolescence and stretching during puberty which leads to an increase in size of particular regions of the body.
4. The increase in the levels of steroid hormones of the body; Cushing's syndrome, local or systemic steroid therapy which have a catabolic effect on fibroblasts.
5. Genetic factors (lack of stretch marks during pregnancy in people who have Ehlers-Danlos syndrome and their presence as one of the diagnostic criteria of lesser importance for Marfan syndrome suggest that genetics play an important role).
6. Stages of immunosuppression associated with pregnancies, medicinal products for pregnancy-induced hypertension, human immunodeficiency virus, or diseases such as tuberculosis and typhoid fever.
7. Associated with chronic liver disease.

Several treatments have been proposed, but none has been consistent. Some authors have suggested that time is the only treatment for SD and that it will return to a normal state in time, which does not seem to be true. It was also suggested some time ago that the most effective stage of treatment for SD is during the active stage, before the scarring process is complete. The first reliable treatment method involved the use of tretinoin cream. Later methods were reported, with variable results, such as Verum (with a preventive effect), Alphastria (with a preventive effect), massages with oils (with a preventive effect), peeling with glycolic and trichloroacetic acid. Laser treatment has recently emerged as an alternative, with 585-nm flashlamp-pumped pulsed dye laser (PDL) being the most widely used type of laser treatment.

With respect to ulcers, ulcerations usually occur in the lower limbs, with an overall prevalence of between 0.18 and 2%, and in patients over 65 years of age, the prevalence is 5%. Most ulcerations in the lower limbs, around 70%, are of the venous type. Arterial-type ulcers of ischemic origin generally make up between 10 and 30%. According to other sources, the prevalence of arterial ulcers in people over 65 years of age is comprised between 8 and 11%. In subjects under 60 years of age, the prevalence is around 2%.

The onset of ulcers of ischemic origin may be due to several factors: they may occur as the result of a cutaneous vasculature condition, which may in turn be due to another underlying disease (chronic venous insufficiency, atherosclerosis, diabetes mellitus, vasculitis, thrombophilia, systemic sclerosis, etc.); on other occasions, they may be the result of a medical or surgical treatment. When the ulcer of ischemic origin occurs at the same time as a treatment applied for treating another disease in the patient, physicians may have to decide whether to interrupt the treatment of this other underlying disease to prevent ulcers, with all the risks and problems this entails.

More general wound care, primarily administered by oral route, are being used for the treatment of ulcers of ischemic origin. Medicinal products for blood pressure, cholesterol, and diabetes, together with aspirin or other anticoagulant or antiplatelet medicinal products, are normally prescribed. In some cases, an angiogram, which is a test consisting of the injection of a contrast dye into the blood vessels, can be performed and special x-rays are taken to identify blockages. In other cases, bypass surgery may be needed to restore blood flow. It should be pointed out that the onset of ulcers of ischemic origin may occur in more common and widespread pathologies with a higher prevalence (as in the case of perniosis), as well as in more serious pathologies (for example, complications arising from diabetes). Some examples are presented below.

Perniosis (erythema pernio, more commonly chilblain), for example, may lead to ulcers of ischemic origin. Perniosis consists of the development of inflammatory, erythematous, and often pruritic lesions, found in acral locations, after contact with the cold. Complications may be local in the form of painful cracking, superinfection, or the formation of real ulcers. There is not a lot of epidemiological data concerning perniosis, but it is very common during seasons with low temperatures and in areas with cold climates. Some papers refer to an incidence of 10% every year in England. In general, it usually affects young women more frequently. Treatment for perniosis primarily focuses on measures for minimizing exposure to cold, reserving pharmacological therapy for those patients who do not improve with these measures. Patients with perniosis are advised to keep the involved area warm using properly insulated clothing, gloves, or footwear, and to avoid exposure to the cold without suitable protection. They are also encouraged to quit smoking due to the harmful effect of tobacco addiction on vascular disease. Data concerning the efficacy of other measures for the perniosis are limited. Topical corticosteroids and nifedipine (indicated for cardiovascular disease) are among the most widely used pharmacological therapies. In clinical practice, medium- to high-potency topical corticosteroids are prescribed in an attempt to accelerate the resolution of lesions caused by perniosis, although no tests have been found to confirm the efficacy of local therapy with corticosteroids. Skin atrophy is a potential adverse effect of this treatment. There have been isolated reports about the use of other therapies, such as the intralesional injection of corticosteroids, oral prednisone, prazosin, pentoxifylline, nicotinamide, topical minoxidil, nitroglycerin paste, and topical tacrolimus. However, more additional studies are needed to determine the efficacy of these therapies.

Diabetes mellitus is another disease in which ulcers may occur, such as diabetic foot ulcers. Some estimates predict that the number of diabetics will increase to over 500 million people in 2035, according to the International Diabetes Federation. Susceptibility to foot ulcers for diabetics varies with age, sex, health, and social factors. Estimates of the annual incidence of diabetic foot ulcers range from 2.5 to 10.7 percent of diabetic patients in developed economies. The incidence may be higher in poor countries due to the lack of education, advanced therapies, or integral healthcare infrastructures. More serious ulcers of the lower limbs may require amputations of the extremities. Amputations arising from complications and inappropriate handling are expensive. In the United States, limb amputations cost about 70,000 $ on average, 30,000 M$ every year for the entire healthcare system. In the EU, amputations may increase the cost of treatment of diabetic foot ulcers to more than 50,000 € (56,687 $) per case.

Systemic sclerosis (or scleroderma) is an autoimmune disease consisting of the accumulation of tissue similar to scar tissue in the skin and in other parts of the body. It also damages the cells covering small artery walls. The global prevalence of this disease is estimated to be 242 cases per million inhabitants per year, and its incidence ranges between 0.6 and 19 cases per million inhabitants per year, and it affects about three times more women as it does men.

As for the main products on the market used to treat skin ulcers, the following are included:
Alprostadil (injections for intravenous administration)
Ketanserin+Benzocaine (gel)
Catalase+Gentamicin sulfate (gel)
Chloramphenicol+Deoxyribonuclease+Fibrinolysin (ointment)
Chlorhexidine hydrochloride+Diphenhydramine+Hydrocortisone acetate (cream)
Clostebol+Neomycin sulfate (cream for topical/vaginal route)
Allantoin (ointment)
Collagenase (ointment)
*Clostridium histolyticum* collagenase+Neomycin sulfate (ointment)
Bendazac (solution for ophthalmic route, tablets for oral route, cream and ointment for topical application)
Bromelain (ointment)
Bucladesine (ointment)
Lysozyme hydrochloride (ointment and patch for topical application)
Nepidermin (ointment)
Polydeoxyribonucleotide (ointment, solution for topical use, intramuscular injection, subcutaneous injection, and solution for ophthalmic administration)
Sodium acexamate (ointment)
Trafermin (spray)
Tretinoin (ointment)
Bovine fibrinolysin+Bovine deoxyribonuclease (ointment)
Trolamine+Sulfacetamide sodium (ointment)

In addition to these products, most of the products sold for this indication are antibiotics and antimicrobials for fighting against potential infections resulting from ulcers. Therefore, they are better described as symptomatic treatments that do not target the causes of the disease. In relation to products being developed for skin ulcers, there are four products in phase II of clinical development, in addition to another eight more products that are still in the pre-clinical phase. Nevertheless, most of them are being developed for pressure ulcers.

Specifically, the following products indicated in the treatment of perniosis (chilblain) have been identified:
Betamethasone valerate+gentamicin sulfate (cream)
Hydrocortisone acetate (cream and emulsion for topical application, aerosol foam for rectal administration)
Pentosan polysulfate sodium (ointment)
Sodium chondroitin sulfate (gel, cream, ointment, and lotion)
Triamcinolone acetonide (cream and ointment)

There are a large number of therapeutic strategies for the aforementioned diseases (stretch marks and skin ulcers), and not any one method has been much more consistent than the rest. Further research and clinical trials are required to define effective new alternatives for these problems and the problems derived from them.

BRIEF DESCRIPTION OF THE INVENTION

A first aspect of the present invention relates to the use of a compound of general formula (I):

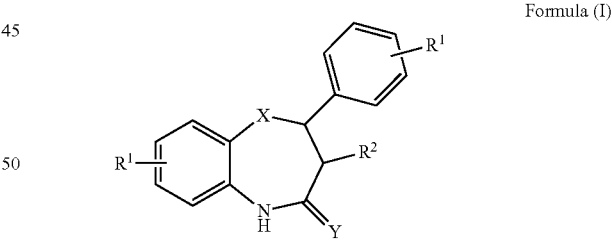

Formula (I)

or any of its salts, preferably any pharmaceutically acceptable salt, pharmaceutically acceptable esters, tautomers, polymorphs, hydrates, or an isomer, prodrugs, derivatives, solvates, or analogs, or any of the combinations thereof, hereinafter compound of the invention, in the production of a medicinal product used to prevent, improve, relieve, and/or treat stretch marks, wherein:

$R^1$ can be present from 0 to 9 times and each $R^1$ is independently selected from the group consisting of optionally substituted linear or branched chain $C_1$-$C_4$ alkyl, cycloalkyl, aryl, or heteroaryl, hydroxy, nitro, amino, halogen, sulfonate, perhaloalkyl, —$OR_4$, —N(R$_4$)$_2$, —CN, —C(=Z)R$_4$, —C(=Z)OR$_4$, —C(=Z)N(R$_4$)$_2$, —N(R$_4$)—C(=Z)R$_4$, —N(R$_4$)—C(=Z)N(R$_4$)$_2$, —OC(=Z)R$_4$, and —SR$_4$, —SOR$_4$, —SO$_2$R$_4$, wherein Z is oxygen or sulfur; and wherein each R$_4$ is independently selected from the group consisting of hydrogen, optionally substituted linear or branched chain C$_1$-C$_5$ alkyl, optionally substituted linear or branched chain C$_2$-C$_5$ alkenyl-alkenyl, C$_2$-C$_5$ alkenyl, optionally substituted linear or branched chain alkynyl, C$_3$-C$_7$ cycloalkyl-cycloalkyl, and C$_5$-C$_{10}$ cycloalkenyl, aryl, or heteroaryl, optionally substituted.

X is selected from the group consisting of oxygen, sulfur, NR$_5$, C(R$_5$)$_2$, wherein R$_5$ is independently selected from the group consisting of hydrogen, optionally substituted linear or branched chain C$_1$-C$_5$, optionally substituted linear or branched chain C$_2$-C$_5$ alkenyl, optionally substituted linear or branched chain C$_2$-C$_5$ alkenyl, C$_3$-C$_7$ cycloalkyl, and C$_5$-C$_{10}$ cycloalkenyl, aryl, or heteroaryl, optionally substituted; or two R$_5$ and X can form C$_3$-C$_7$ cycloalkyl, heterocyclic ring, aryl, or heteroaryl, optionally substituted.

R$_2$ is selected from the group consisting of optionally substituted linear or branched chain C$_1$-C$_4$ alkyl, cycloalkyl, aryl, or heteroaryl, hydroxy, nitro, amino, halogen, sulfonate, perhaloalkyl, —OR$_6$, —N(R$_6$)$_2$, —CN, —C(=Z)R$_6$, —C(=Z)—OR$_6$, —C(=Z)N(R$_6$)$_2$, —N(R$_6$)—C(=Z)R$_6$, —N(R$_6$)—C(=Z)N(R$_6$)$_2$, —OC(=Z)R$_6$, and —SR$_6$, —SOR$_6$, —SO$_2$R$_6$, wherein Z is oxygen or sulfur; and wherein each R$_6$ is independently selected from the group consisting of hydrogen, optionally substituted linear or branched chain C$_1$-C$_5$ alkyl, optionally substituted linear or branched chain C$_2$-C$_5$ alkenyl, optionally substituted linear or branched chain C$_2$-C$_5$ alkynyl, C$_3$-C$_7$ cycloalkyl, and C$_5$-C$_{10}$ cycloalkenyl, aryl, or heteroaryl, optionally substituted.

R$_3$ is selected from the group consisting of optionally substituted linear or branched chain C$_1$-C$_4$ alkyl, cycloalkyl, aryl, or heteroaryl, optionally substituted, —C(=Z)R$_7$, —C(=Z)OR$_7$, and —C(=Z)N(R$_7$)$_2$, wherein Z is oxygen or sulfur; and wherein each R$_7$ is independently selected from the group consisting of hydrogen, optionally substituted linear or branched chain C$_1$-C$_5$ alkyl, optionally substituted linear or branched chain C$_2$-C$_5$ alkenyl, optionally substituted linear or branched chain C$_2$-C$_5$ alkynyl, C$_3$-C$_7$ cycloalkyl, and C$_5$-C$_{10}$ cycloalkenyl, aryl, or heteroaryl, optionally substituted, and Y is oxygen or sulfur.

Alternatively, the first aspect relates to the compound of the invention for the use thereof to prevent, relieve, improve, and/or treat stretch marks.

In a preferred embodiment of this aspect of the invention, the compound is diltiazem, of formula (II), or cis-(+)-[2-(2-dimethylaminoethyl)-5-(4-methoxyphenyl)-3-oxo-6-thia-2-azabicyclo[5.4.0]undeca-7,9,11-trien-4-yl]ethanoate, with CAS number 42399-41-7.

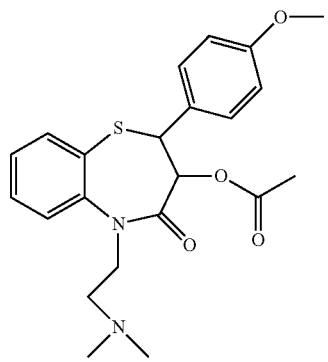

Formula (II)

A second aspect relates to the use of the compound of the invention, or any of its salts, preferably any pharmaceutically acceptable salt, pharmaceutically acceptable esters, tautomers, polymorphs, hydrates, or an isomer, prodrugs, derivatives, solvates, or analogs, or any of the combinations thereof, in the production of a medicinal product used to prevent, improve, relieve, and/or treat skin ulcers. Alternatively, the second aspect relates to the compound of the invention or any of its salts, preferably any pharmaceutically acceptable salt, pharmaceutically acceptable esters, tautomers, polymorphs, hydrates, or an isomer, prodrugs, derivatives, solvates, or analogs, or any of the combinations thereof, for the use thereof to prevent, improve, relieve, and/or treat skin ulcers.

In a preferred embodiment of this aspect of the invention, the skin ulcers are ischemic ulcers. More preferably, they are skin ulcers of ischemic origin having a difficult clinical management.

In another preferred embodiment, the composition of the invention is used for the treatment of diseases presenting with the occurrence of ischemic ulcers. More preferably, the disease presenting with the occurrence of ischemic ulcers is selected from: perniosis, epidermolysis bullosa, venous insufficiency, vasculitis, collagenopathies (such as, but without limitation, systemic lupus erythematosus and systemic scleroderma, for example), ulcers caused by suture dehiscence, post-surgical cutaneous ischemic risk situations (skin flaps or grafts), skin ulcers caused by diabetic microangiopathy (diabetic foot), or any of the combinations thereof.

A third aspect relates to the use of a composition, hereinafter composition of the invention, comprising at least one compound of the invention, or a tautomer, a pharmaceutically acceptable salt, a derivative, or a prodrug thereof, in the production of a medicinal product used to prevent, relieve, improve, and/or treat stretch marks. Alternatively, the third aspect relates to the composition of the invention for the use thereof to prevent, relieve, improve, and/or treat stretch marks.

In a preferred embodiment of this aspect, the composition of the invention is a pharmaceutical composition. In another preferred embodiment of this aspect, the composition of the invention further comprises a pharmaceutically acceptable carrier, or a pharmaceutically acceptable vehicle and/or excipient.

In another preferred embodiment, the composition of the invention is a cosmetic composition.

A fourth aspect relates to the use of the composition of the invention in the production of a medicinal product used to prevent, relieve, improve, and/or treat skin ulcers, alternatively for the use thereof to prevent, relieve, improve, and/or treat skin ulcers.

In a preferred embodiment of this aspect of the invention, the skin ulcers are ischemic ulcers. More preferably, they are skin ulcers of ischemic origin having a difficult clinical management.

In another preferred embodiment, the composition of the invention is used for the treatment of diseases presenting with the occurrence of ischemic ulcers. More preferably, the disease presenting with the occurrence of ischemic ulcers is selected from: perniosis, epidermolysis bullosa, venous insufficiency, vasculitis, collagenopathies (such as, but without limitation, systemic lupus erythematosus and systemic scleroderma, for example), ulcers caused by suture dehiscence, post-surgical cutaneous ischemic risk situations (skin flaps or grafts), skin ulcers caused by diabetic microangiopathy (diabetic foot), or any of the combinations thereof.

DESCRIPTION OF THE DRAWINGS

FIG. 1. Abdominal skin ulcers which entail striae distensae (FIG. 1a) and a skin ulcer cured after treatment with topical diltiazem (Figure ib).

FIG. 2. Patient with perniosis (FIG. 2A). Clinical response after 3 days of applying diltiazem every 12 hours (FIG. 2B).

DETAILED DESCRIPTION OF THE INVENTION

Medical Uses of the Invention

Figure 3A:
FIG. 3. Patient with epidermolysis bullosa with chronic ulcer, 12 month-progression (FIG. 3A). Clinical response after 4 weeks of treatment with diltiazem every 12 hours (FIG. 3B).
Figure 3B:
Figure 4:
FIG. 4. Clinical response of vascular torpid ulcer in the leg.
Figure 5A:
FIG. 5. Suture dehiscence after abdominal surgery (FIG. 5A). Image of the dehiscence with a deep ulcer having congestion in the margins, after three weeks of curing with chlorhexidine and then 2% diltiazem cream every 12 hours (FIG. 5B).
Figure 5B:

The authors of the present invention have found that the treatment of striae distensae and skin ulcers of ischemic origin with 2% diltiazem cream is effective.

Therefore, a first aspect of the present invention relates to the use of a compound of general formula (I):

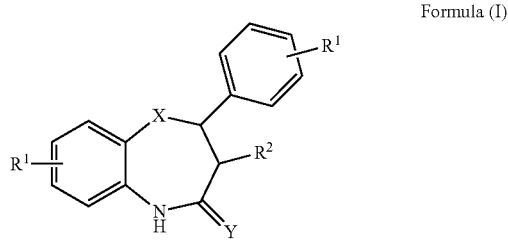

Formula (I)

or any of its salts, preferably any pharmaceutically acceptable salt, pharmaceutically acceptable esters, amides, tautomers, polymorphs, hydrates, or an isomer, prodrugs, derivatives, solvates, or analogs, or any of the combinations thereof, hereinafter compound of the invention, in the production of a medicinal product used to prevent, improve, relieve, and/or treat stretch marks, wherein:

$R^1$ can be present from 0 to 9 times and each $R^1$ is independently selected from the group consisting of optionally substituted linear or branched chain $C_1$-$C_4$ alkyl, cycloalkyl, aryl, or heteroaryl, hydroxy, nitro, amino, halogen, sulfonate, perhaloalkyl, $OR_4$, —$N(R_4)_2$, —CN, —C(=Z)$R_4$, —C(=Z)O$R_4$, —C(=Z)N($R_4$)$_2$, —N($R_4$)—C(=Z)$R_4$, —N($R_4$)—C(=Z)N($R_4$)$_2$, —OC(=Z)$R_4$, and —S$R_4$, —SO$R_4$, —SO$_2$$R_4$, wherein Z is oxygen or sulfur; and wherein each $R_4$ is independently selected from the group consisting of hydrogen, optionally substituted linear or branched chain $C_1$-$C_5$ alkyl, optionally substituted linear or branched chain $C_2$-$C_5$ alkenyl-alkenyl, $C_2$-$C_5$ alkenyl, optionally substituted linear or branched chain alkynyl, $C_3$-$C_7$ cycloalkyl-cycloalkyl, and $C_5$-$C_{10}$ cycloalkenyl, aryl, or heteroaryl, optionally substituted.

X is selected from the group consisting of oxygen, sulfur, $NR_5$, $C(R_5)_2$, wherein $R_5$ is independently selected from the group consisting of hydrogen, optionally substituted linear or branched chain $C_1$-$C_5$, optionally substituted linear or branched chain $C_2$-$C_5$ alkenyl, optionally substituted linear or branched chain $C_2$-$C_5$ alkenyl, $C_3$-$C_7$ cycloalkyl, and $C_5$-$C_{10}$ cycloalkenyl, aryl, or heteroaryl, optionally substituted; or two $R_5$ and X can form $C_3$-$C_7$ cycloalkyl, heterocyclic ring, aryl, or heteroaryl, optionally substituted.

$R_2$ is selected from the group consisting of optionally substituted linear or branched chain $C_1$-$C_4$ alkyl, cycloalkyl, aryl, or heteroaryl, hydroxy, nitro, amino, halogen, sulfonate, perhaloalkyl, —$OR_6$, —$N(R_6)_2$, —CN, —C(=Z)$R_6$, —C(=Z)O$R_6$, —C(=Z)N($R_6$)$_2$, —N($R_6$)—C(=Z) $R_6$, —N($R_6$)—C(=Z)N($R_6$)$_2$, —OC(=Z)$R_6$, and —S$R_6$, —SO$R_6$, —SO$_2$$R_6$, wherein Z is oxygen or sulfur; and wherein each $R_6$ is independently selected from the group consisting of hydrogen, optionally substituted linear or branched chain $C_1$-$C_5$ alkyl, optionally substituted linear or branched chain $C_2$-$C_5$ alkenyl, optionally substituted linear or branched chain $C_2$-$C_5$ alkynyl, $C_3$-$C_7$ cycloalkyl, and $C_5$-$C_{10}$ cycloalkenyl, aryl, or heteroaryl, optionally substituted.

$R_3$ is selected from the group consisting of optionally substituted linear or branched chain $C_1$-$C_4$ alkyl, cycloalkyl, aryl, or heteroaryl, optionally substituted, —C(=Z) $R_7$, —C(=Z)O$R_7$, and —C(=Z)N($R_7$)$_2$, wherein Z is oxygen or sulfur; and wherein each $R_7$ is independently selected from the group consisting of hydrogen, optionally substituted linear or branched chain $C_1$-$C_5$ alkyl, optionally substituted linear or branched chain $C_2$-$C_5$ alkenyl, optionally substituted linear or branched chain $C_2$-$C_5$ alkynyl, $C_3$-$C_7$ cycloalkyl, and $C_5$-$C_{10}$ cycloalkenyl, aryl, or heteroaryl, optionally substituted, and Y is oxygen or sulfur. Alternatively, the first aspect relates to the compound of the invention for the use thereof to prevent, relieve, improve, and/or treat stretch marks.

The term "stretch marks" refers to irregular areas of skin similar to bands, strips, or lines. Stretch marks can be observed as a person grows, rapidly gains weight, or presents certain conditions or diseases. Stretch marks may occur when the skin is stretched too quickly. They can often be observed when the abdomen of a woman gets larger during pregnancy. They can also occur in children who have rapidly become obese. Likewise, they can occur in boys and girls in growth spurts throughout puberty. The most common location of stretch marks can be found on the breasts, hips, thighs, buttocks, abdomen, and sides. Stretch marks occur in the form of parallel lines of reddish, glossy, and thin skin which, over time, become whitish and look like a scar. Stretch marks can be slightly sunken and have a texture that is different from normal skin. They can also present as a result of an abnormal formation of collagen, or as a result of medicines or chemical substances which interfere with the formation thereof. They may likewise be associated with the prolonged use of cortisone compounds, diabetes, Cushing's disease, and the postpartum period. The causes may include any of the following: Cushing's syndrome, Ehlers-Danlos syndrome, pregnancy, puberty, obesity, and/or the excessive use of cortisone-based skin creams (U.S. National Library of Medicine).

In a preferred embodiment of this aspect of the invention, the compound is diltiazem, of formula (II), or cis-(+)-[2-(2-dimethylaminoethyl)-5-(4-methoxyphenyl)-3-oxo-6-thia-2-azabicyclo[5.4.0]undeca-7,9,11-trien-4-yl]ethanoate, of CAS number 42399-41-7.

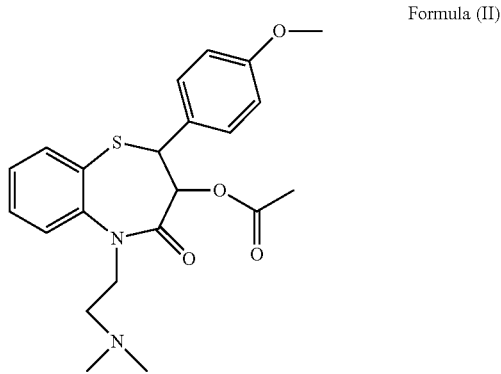 [SMILES: COc1ccc(C2Sc3ccccc3N(CCN(C)C)C(=O)C2OC(C)=O)cc1]

Formula (II)

Throughout the present description, "diltiazem" is not limited to the hydrochloride salt, but rather includes any and all salts that are not hydrochloride salt. Furthermore, "diltiazem" includes the free base compound. As indicated, the scope of the present invention also includes the use of other diastereomers of diltiazem, including the (2R,3S) isomer, (2S,3R) isomer, and (2R,3R) isomer. The scope of the present invention also includes the use of mixtures of any and all of the mentioned isomers, including optically inactive and racemic mixtures.

A second aspect relates to the use of the compound of the invention, or any of its salts, preferably any pharmaceutically acceptable salt, pharmaceutically acceptable esters, amides, tautomers, polymorphs, hydrates, or an isomer, prodrugs, derivatives, solvates, or analogs, or any of the combinations thereof, in the production of a medicinal product used to prevent, improve, relieve, and/or treat skin ulcers. Alternatively, the second aspect relates to the compound of the invention or any of its salts, preferably any pharmaceutically acceptable salt, pharmaceutically acceptable esters, amides, tautomers, polymorphs, hydrates, or an isomer, prodrugs, derivatives, solvates, or analogs, or any of the combinations thereof, for the use thereof to prevent, improve, relieve, and/or treat skin ulcers.

The term "skin ulcers of ischemic origin" refers to ulcers (wounds) occurring on the skin when there is a deficient blood flow. Deficient blood flow causes cell death and tissue damage. Most ischemic ulcers occur on the feet and legs. They are typically slow-healing wounds. Obstructed arteries (atherosclerosis) are the most common cause of ischemic ulcers:

The obstructed arteries prevent the existence of a healthy blood supply to the legs. This means that the tissues in the legs do not receive enough nutrients and oxygen.

The lack of nutrients causes cell death, which damages tissue.

Damaged tissue that does not receive sufficient blood flow also tends to heal more slowly.

Conditions in which the skin is inflamed and fluid builds up in the legs can also cause ischemic ulcers. Often people with poor circulation also have nerve damage or ulcers in the feet due to diabetes. The nerve damage makes it harder to feel an area of a shoe that rubs against the foot and causes an ulcer or sore. Once an ulcer is formed, the lack of blood flow makes it difficult to heal (U.S. National Library of Medicine).

Preferably, the ischemic ulcers are secondary to arterial insufficiency, venous insufficiency, microcirculation defects (like in diabetes, in rheumatologic diseases such as scleroderma, etc), primary or secondary states of thrombophilia or hypercoagulability (due to tumors, rheumatologic diseases such as systemic lupus, etc.), or they can be due to iatrogenesis (secondary to antiangiogenic medical treatments or to surgical or invasive procedures, such as catheterizations, etc In a preferred embodiment of this aspect of the invention, the skin ulcers are ischemic ulcers. More preferably, they are skin ulcers of ischemic origin having a difficult clinical management.

In another preferred embodiment, the composition of the invention is used for the treatment of diseases presenting with the occurrence of ischemic ulcers. More preferably, the disease presenting with the occurrence of ischemic ulcers is selected from: perniosis, epidermolysis bullosa, venous insufficiency, vasculitis, collagenopathies (such as, but without limitation, systemic lupus erythematosus and systemic scleroderma, for example), ulcers caused by suture dehiscence, post-surgical cutaneous ischemic risk situations (skin flaps or grafts), skin ulcers caused by diabetic microangiopathy (diabetic foot), or any of the combinations thereof.

A third aspect relates to the use of a composition, hereinafter composition of the invention, comprising at least one compound of the invention, or a tautomer, a pharmaceutically acceptable salt, a derivative, or a prodrug thereof, in the production of a medicinal product used to prevent, relieve, improve, and/or treat stretch marks. Alternatively, the third aspect relates to the composition of the invention for the use thereof to prevent, relieve, improve, and/or treat stretch marks.

In a preferred embodiment, the composition of the invention comprises the compound of the invention as the only active ingredient, although it may comprise other pharmaceutically acceptable vehicles and excipients.

In another preferred embodiment of this aspect, the composition of the invention is a pharmaceutical composition. In another preferred embodiment of this aspect, the composition of the invention further comprises a pharmaceutically acceptable carrier, or a pharmaceutically acceptable vehicle and/or excipient.

In another preferred embodiment, the composition of the invention is a cosmetic composition. The cosmetic composition may comprise cosmetically acceptable excipients.

A fourth aspect relates to the use of the composition of the invention in the production of a medicinal product used to prevent, relieve, improve, and/or treat skin ulcers, alternatively, for the use thereof to prevent, relieve, improve, and/or treat skin ulcers.

In a preferred embodiment of this aspect of the invention, the skin ulcers are ischemic ulcers. More preferably, they are skin ulcers of ischemic origin having a difficult clinical management.

In another preferred embodiment, the composition of the invention is used for the treatment of diseases presenting with the occurrence of ischemic ulcers. More preferably, the disease presenting with the occurrence of ischemic ulcers is selected from: perniosis, epidermolysis bullosa, venous insufficiency, vasculitis, collagenopathies (such as, but without limitation, systemic lupus erythematosus and systemic scleroderma, for example), ulcers caused by suture dehiscence, post-surgical cutaneous ischemic risk situations (skin flaps or grafts), skin ulcers caused by diabetic microangiopathy (diabetic foot), or any of the combinations thereof.

In a preferred embodiment, the composition of the invention comprises the compound of the invention as the only active ingredient, although it may comprise other pharmaceutically acceptable vehicles and excipients.

In another preferred embodiment of this aspect, the composition of the invention is a pharmaceutical composition. In another preferred embodiment of this aspect, the composition of the invention further comprises a pharmaceutically acceptable carrier, or a pharmaceutically acceptable vehicle and/or excipient.

Cosmetic Uses of the Invention

In another preferred embodiment, the composition of the invention is a cosmetic composition. The cosmetic composition may comprise cosmetically acceptable excipients.

Therefore, another aspect of the invention relates to a cosmetic composition, hereinafter cosmetic composition of the invention for the use thereof in skin atrophies. Preferably, the skin atrophies are stretch marks. More preferably, the stretch marks are selected from striae albicans, striae atrophicae, and striae distensae.

Stretch marks appearing after pregnancy, weight gain, or due to disease and medication are known by the name striae distensae. They have been given several names, are classified as L90.6 in the CIE-10, and include striae albicans, striae atrophicae, and striae distensae, per se.

The compounds of the present invention represented by formulas (I) and/or (II) can include isomers, depending on the presence of multiple bonds, including optical isomers or enantiomers, depending on the presence of chiral centers. Individual isomers, enantiomers, or diastereoisomers and mixtures thereof fall within the scope of the present invention, i.e., the term isomer also refers to any mixture of isomers, such as diastereomers, racemates, etc., even the optically active isomers thereof or mixtures in different proportions thereof. Individual enantiomers or diastereoisomers, as well as mixtures thereof, can be separated by means of conventional techniques.

Prodrugs of the compounds of formula (I) and/or (II) are also fall within the scope of this invention. As it is used herein, the term "prodrug" includes any derivative of a compound of formula (I) and/or (II), for example and in a non-limiting manner: esters (including carboxylic acid esters, amino acid esters, phosphate esters, sulfonate esters of metal salts, etc.), carbamates, amides, etc., which, when administered to an individual, can be converted directly or indirectly into said compound of formula (I) and/or (II) in the mentioned individual. Advantageously, said derivative is a compound which increases the bioavailability of the compound of formula (I) and/or (II) when administered to an individual or enhances the release of the compound of formula (I) and/or (II) into a biological compartment. The nature of said derivative is not critical as long as that it can be administered to an individual and provide the compound of formula (I) in a biological compartment of an individual. Said prodrug can be prepared by means of conventional methods known to those skilled in the art.

As it is used herein, the term "derivative" includes both pharmaceutically acceptable compounds, i.e., derivatives of the compound of formula (I) and/or (II) which can be used in the production of a medicinal product or food compositions, and non-pharmaceutically acceptable derivatives, since they may be useful in the preparation of pharmaceutically acceptable derivatives.

The compounds of the invention can be in crystalline form as free compounds or solvates. In this sense, as it is used herein the term "solvate" includes both pharmaceutically acceptable solvates, i.e., solvates of the compound of formula (I) and/or (II) which can be used in the production of a medicinal product, and non-pharmaceutically acceptable solvates, which may be useful in the preparation of pharmaceutically acceptable solvates or salts. The nature of the pharmaceutically acceptable solvate is not critical as long as it is pharmaceutically acceptable. In a particular embodiment, the solvate is a hydrate. Solvates can be obtained by conventional solvation methods known to those skilled in the art.

For application in therapy, the compounds of formula (I) and/or (II), their salts, prodrugs, or solvates will preferably be in a pharmaceutically acceptable or substantially pure form, i.e., having a pharmaceutically acceptable level of purity, excluding the normal pharmaceutical additives such as diluents and carriers, and not including materials considered toxic at normal dosage levels. The levels of purity of the active ingredient are preferably greater than 50%, more preferably greater than 70%, and still more preferably greater than 90%. In a preferred embodiment, the levels of purity of the compound of formula (I), or its salts, solvates, or prodrugs are greater than 95%.

The pharmaceutically acceptable adjuvants and vehicles which can be used in the compositions of the invention are the adjuvants and vehicles known to those skilled in the art and commonly used in the production of therapeutic compositions.

In the sense used in this description, the expression "therapeutically effective amount" refers to the amount of the agent or compound capable of developing the therapeutic action determined by its pharmacological properties, which is calculated to produce the desired effect, and it will generally be determined by, among other causes, the characteristics typical of the compounds, including patient age and condition, the severity of the alteration or disorder, and the administration route and frequency.

In a preferred embodiment, the compositions of the invention comprise the compound of the invention in a proportion of between 0.1% and 10%, more preferably between 0.5% and 7.5%, even more preferably between 1% and 5%, and even much more preferably between 1.5% and 2.5% by weight. In a particular embodiment of the invention, the proportion of the compound of the invention in the composition of the invention is about 2% by weight. More preferably, the compound of the invention is diltiazem. In another preferred embodiment, the composition of the invention comprises the compound of the invention as the only active ingredient, although it may comprise pharmaceutically acceptable vehicles and/or excipients. More preferably, the compound of the invention is at the concentrations described above, and even more preferably, the compound of the invention is diltiazem.

The compounds described in the present invention, its salts, prodrugs, and/or solvates, as well as the pharmaceutical compositions containing them can be used together with other additional drugs or active ingredients to provide a combination therapy. Said additional drugs can be part of the same pharmaceutical or cosmetic composition, alternatively, they can be provided in the form of a separate composition so that it may or may not be administered simultaneously with respect to the pharmaceutical or cosmetic composition, comprising a compound of formula (I) or of formula (II), or a salt, prodrug, or solvate thereof.

Therefore, in another preferred embodiment, the pharmaceutical or cosmetic composition further comprises another active ingredient. Preferably, this active ingredient is a moisturizing and/or firming active ingredient. The moisturizing active ingredient can be formulated with humectants, molecules with occlusion capacity and/or lipids. On the other hand, firming active ingredients are characterized by including elastin and collagen in their formulation, in addition to plant extracts with the various regenerating, tensing, and stimulating functions of proteosynthesis. The formulations of firming cosmetics are usually made up of active ingredients which regenerate the connective tissue, and tensing active ingredients, in addition to the aforementioned moisturizing active ingredients.

More preferably, the active ingredient is selected from the list consisting of: glycerin, propylene glycol, sorbitol, low molecular weight polyethylene glycols (PEG 400), acetamide derivatives, glucose ethers, betaine, saccharide isomerate, beeswax, lanolin, petrolatum, natural moisturizing factor analogs (pyrrolidine carboxylic acid, urea, lactic acid/sodium lactate, sugars, allantoin), lactic salts collagen, elastin, hyaluronic acid, chitosan, galactomannan, silicon, *Echinacea angustifolia, Mimosa tenuiflora*, or Tepezcohuite extract, avocado oil and shea butter unsaponifiables, Indian pennywort and/or vitamin A or retinol and/or vitamin E As it is used herein, the terms "active ingredient," "active substance," "pharmaceutically active substance," or "pharmaceutically active ingredient" means any component which may provide pharmacological activity or another different effect in the diagnosis, cure, mitigation, treatment, or prevention of a disease, or which affects the body structure or function of humans or other animals. The term includes those components that promote a chemical change in the production of the drug and are present in the drug in an envisaged modified form, providing the specific activity or effect.

Dosage Forms of the Invention

Another aspect of the invention relates to a dosage form, hereinafter dosage form of the invention, comprising the compound of the invention or the composition of the invention.

In this specification, "dosage form" is understood to mean the mixture of one or more active ingredients, with or without additives, having physical characteristics for suitable dosing, preservation, administration, and bioavailability.

In another preferred embodiment of the present invention, the pharmaceutical compositions and dosage forms of the invention are suitable for topical administration. The possible forms for topical administration are, without limitation, plaster, ointment, paste, cream, solution, suspension, emulsion, lotion, liniment, gel, hydrogel, hydrocolloid, foam, powder, or any of the combinations thereof.

A "plaster" or "patch" is a dosage form consisting of a solid or semisolid form which contains the active ingredient/ingredients and additive/additives extended on a piece of fabric, plastic, or adhesive strip, serving as a support and protection, in addition to furnishing an occlusive and macerating action that further allows direct contact with the skin and softens with body temperature.

An "ointment" or "salve" is a dosage form consisting of a preparation having a soft consistency which contains active ingredient/ingredients and additive/additives incorporated to a suitable base that imparts mass and consistency thereto. It is applied on the skin and mucosae and adheres to same. This base can be fat- or water-soluble, generally anhydrous, or with a maximum of 20% water. It is also referred to as a hydrophilic ointment when it contains a base that can be washed away or removed with water.

A "paste" is a dosage form consisting of a semisolid form which contains active ingredient/ingredients and additive/additives, prepared based on a high concentration of insoluble powders (20% to 50%), in weak abrasive or absorbent fatty or aqueous bases combined with soaps.

A "cream" is a dosage form consisting of a liquid or semisolid preparation which contains active ingredient/ingredients and additive/additives required for obtaining an emulsion, generally an oil-in-water emulsion, with a water content greater than 20%.

A "solution" is a dosage form consisting of a transparent and homogeneous liquid preparation that is obtained by dissolving active ingredient/ingredients and additive/additives in water and intended for external or internal use. Injectable solutions as well as solutions intended for the eyes and ears must be sterile solutions.

A "suspension" is a dosage form consisting of a dispersed system made up of two phases which contain active ingredient/ingredients and additive/additives. One of the phases, the continuous or external phase is generally a liquid or semisolid and the dispersed or internal phase is made up of solids (active ingredients) that are insoluble but dispersible in the external phase. Injectable suspensions must be sterile.

An "emulsion" is a dosage form consisting of a heterogeneous system, generally made up of two liquids not miscible with one another, in which the dispersed phase is made up of small globules distributed in a vehicle in which they are not miscible. The dispersed phase is also known as internal phase and the dispersion means is known as external or continuous phase. Emulsions include water-in-oil or oil-in-water emulsions and they can be presented as semisolids or liquids. The active ingredient/ingredients and additive/additives can be in the external or internal phase.

A "lotion" is a dosage form which can be presented as a solution, suspension, or emulsion that contains active ingredient/ingredients and additive/additives, and the dispersing agent of which is mainly water.

A "liniment" is a dosage form consisting of a presentation in the form of a liquid, solution, or emulsion containing active ingredient/ingredients and additive/additives, with an aqueous, alcoholic, or fatty vehicle.

A "jelly" is a dosage form consisting of a semisolid colloid which contains active ingredient/ingredients and additive/additives, the water-soluble base of which generally consists of gums such as gum tragacanth; other bases used are: glycerin, pectin, alginates, boroglycerine compounds, synthetic derivatives or natural substances such as carboxymethyl cellulose.

A "gel" is a dosage form consisting of a semisolid preparation which contains active ingredient/ingredients and additive/additives, solids in a liquid which can be water, alcohol, or oil, such that a network of particles trapped in the liquid phase is formed.

Hydrogels are systems in colloidal state that look like a solid, such as heat-coagulated albumin, gelatin that is gelled by cooling, etc. One of the properties of hydrogels is the swelling and increase of volume due to the absorption of water and the substances dissolved therein, which is property shared by all tissues in organisms formed by colloidal materials.

"Colloids" are materials formed by a dispersed phase (matrix) and a dispersing phase (filling). When the dispersing phase is water, it is referred to as a "hydrocolloid". They are characterized in that they can coagulate (transition from solution to solid gel) if the dispersed phase is abundant, and flocculate (transition from gel to solution) when the dispersed phase is scarce.

The dosage forms of the invention preferably comprise the compound of the invention in a proportion of between 0.1% and 10%, more preferably between 0.5% and 7.5%, even more preferably between 1% and 5%, and even much more preferably between 1.5% and 2.5% (by weight). In a particular embodiment of the invention, the proportion of the compound of the invention in the composition of the invention is about 2% (by weight). More preferably, the compound of the invention is diltiazem. In another preferred embodiment, the composition of the invention comprises the compound of the invention as the only active ingredient, although it may comprise pharmaceutically acceptable vehicles and/or excipients. More preferably, the compound of the invention is at the concentrations described above, and even more preferably, the compound of the invention is diltiazem.

The aforementioned formulations can be prepared using conventional methods, such as those described in the Pharmacopoeias of different countries and in other reference texts.

As it is used herein, the term "medicinal product" refers to any substance used to prevent, diagnose, relieve, treat, or cure diseases in humans and animals.

The compounds, compositions, or dosage forms of the present invention can be administered by means of any suitable method, such as intravenous infusion and through the oral, topical, or parenteral routes. Topical administration is preferred due to its convenience for patients and due to the nature of the diseases to be treated.

The administered amount of a compound of the present invention will depend on the relative efficacy of the chosen compound, the severity of the disease to be treated, and the weight of the patient. However, the compounds of this invention will be administered one or more times a day, for example 1, 2, 3, or 4 times a day, with a total dose between 0.1 and 1000 mg/kg/day. It is important to take into account that it may be necessary to vary the dose, depending on the patient's age and condition, as well as modify the administration route.

The compounds and compositions of the present invention can be used together with other medicinal products in combined therapies. The other drugs may be part of the same composition or of another different composition, for administration at the same time or at different times.

Throughout the description and claims, the word "comprises" and variants thereof do not intend to exclude other technical features, additions, components, or steps. For those skilled in the art, other objects, advantages, and features of the invention will be inferred in part from the description and in part from the practice of the invention. The following examples and figures are provided by way of illustration and do not intend to be limiting of the present invention.

EXAMPLES OF THE INVENTION

Example 1

This example relates to the case of an 11-year old child with a 5-year history of resectable astrocytomas (grade II) involving the left cerebellopontine angle. The initial treatment consisted of observation spanning 2 years, due to the clinical and radiological stability of the tumor. Then the disease progressed and the patient received sequential treatment with 4 different lines of chemotherapy: temozolomide, TPCV (thioguanine-procarbazine-lomustine-vincristine), vinblastina, and cisplatin-irinotecan, for three, five, two, and four months, respectively. On the other hand, the patient also received local radiation therapy with a total dose of 54 Gy. In this patient, control with these treatments was not attained, the disease progressed, and the symptoms worsened. Said symptoms consisted of hiccups, dysphagia, and dysmetria. For control of the symptoms, the patient received prolonged treatment with high doses of dexamethasone and developed multiple violet-colored striae distensae on his abdomen. Finally, the patient started treatment with bevacizumab at 10 mg/kg every 2 weeks, achieving stability and control of the radiological signs, although he continued to require systemic corticotherapy. After 20 months of treatment with bevacizumab (40 cycles), the patient developed skin ulcers involving three striae distensae induced by corticosteroids (FIG. 1a).

Diltiazem was considered a therapeutic possibility for the patient. The Pharmacy Commission (Comisión de Farmacia) of the hospital approved the compassionate use of the drug and parental consent was obtained. The decision was made to continue treatment with bevacizumab due to the important benefit of the drug for this patient, since it was the only treatment that controlled the symptomatology and progression of the tumor.

The patient was treated with 2% diltiazem cream twice a day and his wounds were cared for with polyurethane dressings. The response to treatment with diltiazem was excellent. The ulcers were completely healed in four weeks (FIG. 1b), without having to suspend bevacizumab. After the suspension of topical diltiazem, the patient developed a new ulcerated lesion located in the stretch marks which was resolved by treating it again with diltiazem. After 9 months of follow-up, the patient continues undergoing treatment with bevacizumab, has reached radiological stability and is ulcer-free.

Example 2

This example relates to a patient who has had perniosis on the hands for many years with occurrence of painful outbreaks and pruritus during cold seasons. The patient seeks medical attention for lesions due to perniosis on the hands with a number of painful, cracked, erythematous-violaceous lesions. Treatment with 2% diltiazem cream every 12 hours is started, and complete resolution of the lesions and symptomatology can be seen after three days of treatment.

Example 3

This example relates to a 3-year old male patient with recessive dystrophic epidermolysis bullosa and a chronic ulcer in the pectoral region with progression of more than a year with daily pain and exudation. Treatment with 2% diltiazem cream every 12 hours is started, and the patient shows good tolerance and partial response after 4 weeks of treatment.

Example 4

This example relates to a patient with systemic lupus erythematosus who for years has had a vascular torpid ulcer on his leg that does not go away with the usual cures. Treatment with 2% diltiazem cream is started, and after six months complete resolution of the ulcer is achieved.

Example 5

This example relates to a 2-week old newborn presenting suture dehiscence after abdominal surgery on a lymphatic malformation. After 7 days of progression without any improvement to dehiscence with the usual cures, treatment with 2% diltiazem cream every 12 hours is started until achieving a complete resolution of the dehiscence after 3 weeks of treatment.

The invention claimed is:

1. A method for treating stretch marks in a subject in need thereof, the method comprising administering a therapeutically effective amount of a compound of formula (I):

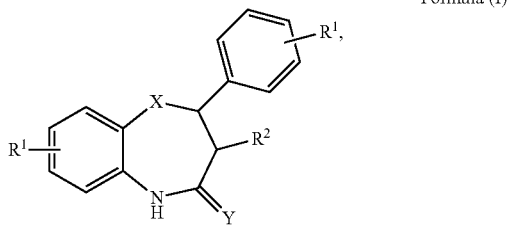

Formula (I)

or a pharmaceutically acceptable salt thereof, to the subject, wherein:
   $R^1$ is present from 0 to 9 times and each $R^1$ is independently selected from the group consisting of linear or branched chain $C_1$-$C_4$ alkyl, cycloalkyl, aryl, hydroxy, nitro, amino, halogen, sulfonate, perhaloalkyl, —$OR_4$, —$N(R_4)_2$, —CN, —C(=Z)$R_4$, —C(=Z)$OR_4$, —C(=Z)$N(R_4)_2$, —$N(R_4)$—C(=Z)$R_4$, —$N(R_4)$—C(=Z)$N(R_4)_2$, —OC(=Z)$R_4$, —$SR_4$, —$SOR_4$, and —$SO_2R_4$, wherein Z is oxygen or sulfur; and wherein each $R_4$ is independently selected from the group consisting of hydrogen, linear or branched chain $C_1$-$C_5$ alkyl, linear or branched chain $C_2$-$C_5$ alkenyl-alkenyl, $C_2$-$C_5$ alkenyl, linear or branched chain alkynyl, $C_3$-$C_7$ cycloalkyl-cycloalkyl, $C_5$-$C_{10}$ cycloalkenyl, and aryl;
   X is selected from the group consisting of oxygen, sulfur, $NR_5$, and $C(R_5)_2$, wherein $R_5$ is independently selected from the group consisting of hydrogen, linear or branched chain $C_1$-$C_5$, linear or branched chain $C_2$-$C_5$ alkenyl, linear or branched chain $C_2$-$C_5$ alkenyl, $C_3$-$C_7$ cycloalkyl, and $C_5$-$C_{10}$ cycloalkenyl, and aryl, or two $R_5$ form $C_3$-$C_7$ cycloalkyl, or aryl;
   $R_2$ is selected from the group consisting of linear or branched chain $C_1$-$C_4$ alkyl, cycloalkyl, aryl, hydroxy, nitro, amino, halogen, sulfonate, perhaloalkyl, —$OR_6$, —$N(R_6)_2$, —CN, —C(=Z)$R_6$, —C(=Z)$OR_6$, —C(=Z)$N(R_6)_2$, —$N(R_6)$—C(=Z)$R_6$, —$N(R_6)$—C(=Z)$N(R_6)_2$, —OC(=Z)$R_6$, —$SR_6$, —$SOR_6$, and —$SO_2R_6$, wherein Z is oxygen or sulfur; and wherein each $R_6$ is independently selected from the group consisting of hydrogen, linear or branched chain $C_1$-$C_5$ alkyl, linear or branched chain $C_2$-$C_5$ alkenyl, linear or branched chain $C_2$-$C_5$ alkynyl, $C_3$-$C_7$ cycloalkyl, $C_5$-$C_{10}$ cycloalkenyl, and aryl;
   $R_3$ is selected from the group consisting of linear or branched chain $C_1$-$C_4$ alkyl, cycloalkyl, aryl, —C(=Z)$R_7$, —C(=Z)$OR_7$, and —C(=Z)$N(R_7)_2$, wherein Z is oxygen or sulfur; and wherein each $R_7$ is independently selected from the group consisting of hydrogen, linear or branched chain $C_1$-$C_5$ alkyl, linear or branched chain $C_2$-$C_5$ alkenyl, linear or branched chain $C_2$-$C_5$ alkynyl, $C_3$-$C_7$ cycloalkyl, $C_5$-$C_{10}$ cycloalkenyl, and aryl; and
   Y is oxygen or sulfur.

2. The method of claim 1, wherein the compound is diltiazem having the structure of formula (II):

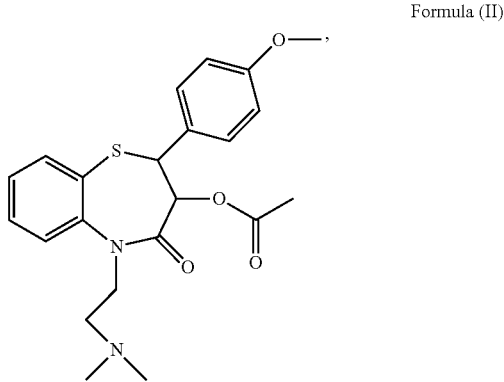 [SMILES: COc1ccc(C2Sc3ccccc3N(CCN(C)C)C(=O)C2OC(C)=O)cc1]

Formula (II)

or a pharmaceutically acceptable salt thereof.

3. The method of claim 1, wherein the compound is administered in a pharmaceutical composition at a concentration of between 0.1% and 10% by weight.

4. The method of claim 3, wherein the compound is at a concentration of about 2% by weight.

5. The method of claim 1, wherein the compound is diltiazem.

6. The method of claim 1, further comprising administering another active ingredient.

7. The method of claim 1, wherein the compound is administered in a unit dosage form.

8. The method of claim 7, wherein the unit dosage form is selected from plaster, ointment, paste, cream, solution, suspension, emulsion, lotion, liniment, gel, hydrogel, hydrocolloid, foam, powder, and combinations thereof.

9. The method of claim 1, wherein the compound is administered in a pharmaceutical composition at a concentration of between 0.5% and 7.5% by weight.

10. The method of claim 1, wherein the compound is administered in a pharmaceutical composition at a concentration of between 1% and 5% by weight.

11. The method of claim 1, wherein the compound is administered in a pharmaceutical composition at a concentration of between 1.5% and 2.5% by weight.

* * * * *